United States Patent
Schatzmayr et al.

(10) Patent No.: US 9,586,990 B2
(45) Date of Patent: Mar. 7, 2017

(54) ENZYMES FOR TRANSFORMING ERGOPEPTINES AND METHOD THEREFOR

(71) Applicant: Erber Aktiengesellschaft, Herzogenburg (AT)

(72) Inventors: Gerd Schatzmayr, Tulln (AT); Eva-Maria Binder, Tulln (AT); Michaela Thamhesl, Koenigsdorf (AT); Dieter Moll, Stockerau (AT)

(73) Assignee: ERBER AKTIENGESELLSCHAFT, Herzogenburg (AT)

( * ) Notice: Subject to any disclaimer, the term of this patent is extended or adjusted under 35 U.S.C. 154(b) by 0 days.

(21) Appl. No.: 14/434,219

(22) PCT Filed: Oct. 4, 2013

(86) PCT No.: PCT/AT2013/000161
§ 371 (c)(1),
(2) Date: Apr. 8, 2015

(87) PCT Pub. No.: WO2014/056006
PCT Pub. Date: Apr. 17, 2014

(65) Prior Publication Data
US 2015/0274775 A1    Oct. 1, 2015

(30) Foreign Application Priority Data
Oct. 9, 2012 (AT) .................. A 1091/2012

(51) Int. Cl.
C07K 5/083 (2006.01)
C12P 17/18 (2006.01)
C12N 9/14 (2006.01)
C12N 9/52 (2006.01)

(52) U.S. Cl.
CPC ............ *C07K 5/0806* (2013.01); *A23K 10/14* (2016.05); *C12N 9/14* (2013.01); *C12N 9/52* (2013.01); *C12P 17/183* (2013.01); *Y02P 20/52* (2015.11)

(58) Field of Classification Search
None
See application file for complete search history.

(56) References Cited

FOREIGN PATENT DOCUMENTS

FR    1362876 A    6/1964

OTHER PUBLICATIONS

Martinkova, L., Kren, V., Cvak, L., Ovesna, M. & Prepechalova, I. 2000. Hydrolysis of lysergamide to lysergic acid by *Rhodococcus equi* A4. J.Biotechnol., 84, 63-66, Nov. 17, 2000.
Kourist, R., Jochens, H., Bartsch, S., Kuipers, R., Padhi, S.K., Gall, M., Böttcher, D., Joosten, H.-J. & Bornscheuer, U. T. 2010, The α/β Hydrolase Fold 3DM Database (ABHDB) as a Tool for Protein Engineering. ChemBioChem, 11, 1635-1643.
Ollis, D. L., Cheah, E., Cygler, M., Dijkstra, B., Frolow, F., Franken, S.M., Harel, M., Remington, S.J., Silman, I. & Schrag, J. The alpha/beta hydrolase fold. Protein Eng., 5, 197-211, Jan. 1, 1992.
Schardl C. L., Panaccione D. G. & Tudzynski P. 2006. Ergot Alkaloids—Biology and Molecular Biology. The Alkaloids, 63, 45-86.
Yamada Y., Matsuda M., Maeda K. & Mikata K. 1995. The Phylogenetic Relationship of Methanol-assimilating Yeasts Based on the Partial Sequence of 18S and 26S Ribosomal RNAs: The Proposal of *Komagataella* Gen. Nov. (Saccharomycetaceae). Biosci. Biotech. Biochem., 59(3), 439-444.
Lucas S et al., Alpha/beta hydrolase fold protein from *Geobacillus* sp, UniProt, Database accession No. D3E991, Mar 23, 2010.

*Primary Examiner* — Nashaat Nashed
(74) *Attorney, Agent, or Firm* — Jacobson Holman, PLLC.

(57) ABSTRACT

Enzymes for transforming, in particular hydrolytically cleaving, ergopeptines, which ergopeptines are α/β-hydrolases hydrolytically cleaving ergopeptines in the cyclol ring, for the transformation of ergopeptines, and method for producing ergopeptine-metabolizing enzymes.

2 Claims, 4 Drawing Sheets

Figure 1:
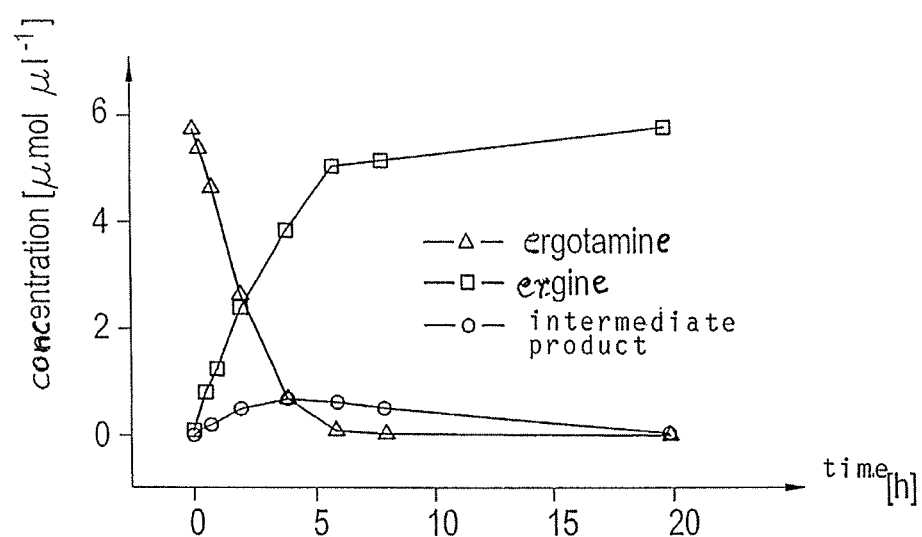

Fig. 2
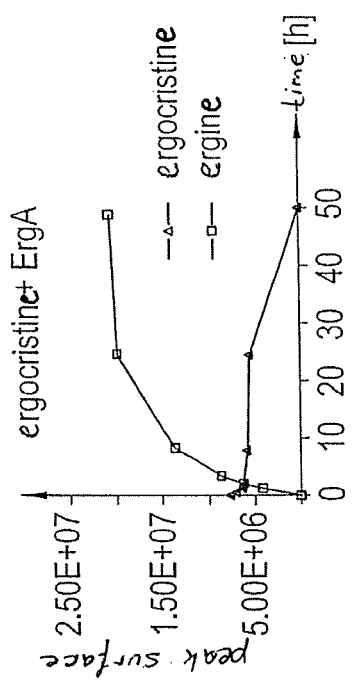
Fig. 2b
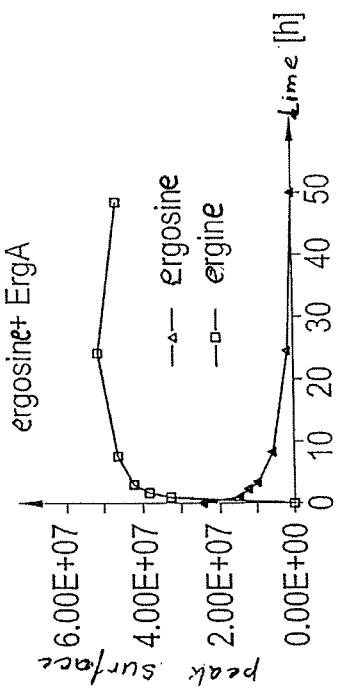
Fig. 2d
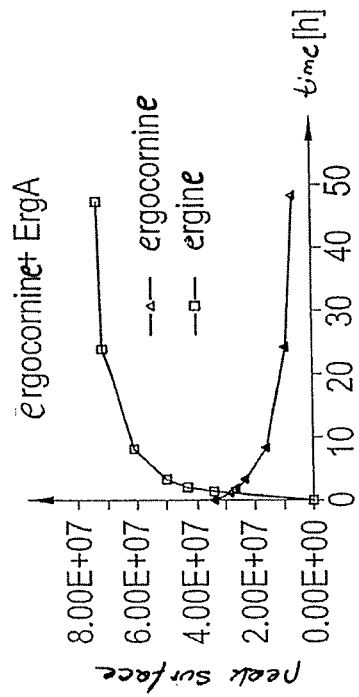
Fig. 2a
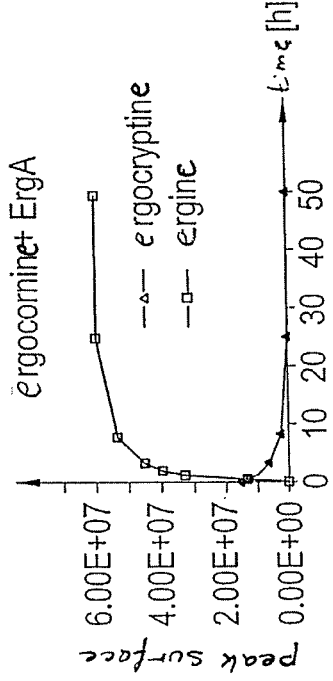
Fig. 2c

ENZYMES FOR TRANSFORMING ERGOPEPTINES AND METHOD THEREFOR

The present invention relates to enzymes for transforming, in particular hydrolytically cleaving, ergopeptines, a method for transforming ergopeptines, and a method for producing ergopeptine-metabolizing enzymes.

BACKGROUND OF THE INVENTION

Ergopeptines are a group of ergot alkaloids and are, moreover, secondary metabolic products formed by plant-associated fungi of the genus *Claviceps* belonging to the Clavicipitaceae family.

The most prominent member of this genus is *Claviceps purpurea*, which above all affects cereals like rye, wheat, tricitale, barley and maize. Another member, namely *Claviceps africana*, is widely found in millet. Further ergot alkaloid-producing fungi of this family include grass endophytes of the genus *Epichloë*, *Neotyphodium* and *Balansia*, yet also *Aspergillus fumigatus* and various *Penicillium* spp. are able to produce ergot alkaloids.

In general, ergot alkaloids have a characteristic skeletal structure with a tetracyclic ergoline ring that comprises a methylated nitrogen at the 6-position and may have different substituents at the C-8 position. Based on these substituents, ergot alkaloids are categorized into clavines, simple lysergic acid amides, ergopeptines and ergopeptams.

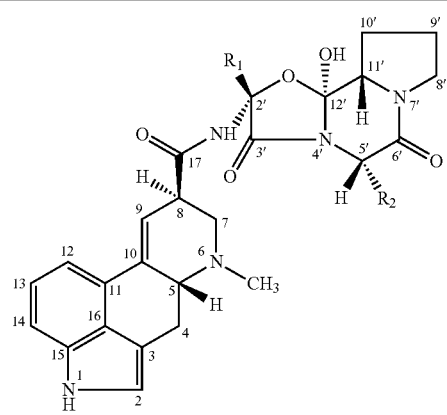

| R1 | R2 | Ergopeptine |
|---|---|---|
| CH$_3$ | CH(CH$_3$)$_2$ | Ergovaline |
| CH$_3$ | CH$_2$C$_6$H$_5$ | Ergotamine |
| CH$_3$ | CH$_2$CH(CH$_3$)$_2$ | α-Ergosine |
| CH(CH$_3$)$_2$ | CH(CH$_3$)$_2$ | Ergocomine |
| CH(CH$_3$)$_2$ | CH$_2$C$_6$H$_5$ | Ergocrystine |
| CH(CH$_3$)$_2$ | CH$_2$CH(CH$_3$)$_2$ | α-Ergocryptine |

Due to their structural similarity with neurotransmitters, ergot alkaloids interact with the receptors of the latter, causing a plurality of effects such as intoxications, yet also positive actions in the pharmaceutical field. Today, ergot alkaloids no longer constitute problems in the human field because of improved cleaning techniques in mills. However, they still contribute to problems in animal husbandry, causing a plurality of adverse symptoms. The symptoms caused by ergot alkaloids in animals, in particular, comprise gangrene, lameness, a reduced weight gain, an increased respiratory frequency, a reduced serum prolactin level, a reduced milk production, and a low reproduction rate. In this respect, the endophytes encountered in pasture grasses in America, New Zealand and Australia first of all raise problems in animal husbandry. Thus, the endophyte infection of tall fescue by Neotyphodium coenophialum has caused high losses to livestock producers.

For the majority of the above-described effects or symptoms, ergopeptines, which constitute the group with the highest multiformity of the ergot alkaloids, are responsible, which, in turn, are themselves categorized according to the amino acid directly bound to D-lysergic acid. In this respect, the characteristic oxazolidin-4-ring of the ergopeptines is referred to as cyclol ring according to the nomenclature used by Schardl et al. Members are represented by the ergotamine group comprising, inter alia, ergotamine, ergovaline and ergosine, in which the first amino acid is L-alanine. A further group is the ergotoxine group, in which the first amino acid bound to D-lysergic acid is L-valine. Representatives of the latter include ergocristine, ergocryptine or ergocomine. Still a further member is the ergoxine group, in which the first amino acid bound to lysergic acid is an α-aminobutyric acid. Representatives are ergostine and ergonine.

Among these, ergovaline is one of the main alkaloids of the Neotyphodium and Epichloë species endophytically growing in pasture grasses and is of veterinary-toxicological relevance, e.g. in fescue toxicosis. 9,10-dihydroergopeptines only rarely occur in nature and have so far only been detected in *Sphacelia sorghi*. Partially synthetically obtained dihydroergopeptines such as dihydroergotamine and dihydroergotoxine have therapeutic relevance in the treatment of migraine and cardiovascular diseases. Apart from the described positive effects, in particular the therapeutic relevance of ergopeptines, their toxic action is, however, of non-negligible significance, since, in particular, their toxicity due, for instance, to the consumption of contaminated grains or toxic endophytes will result in the destruction or impairment or damage of numerous physiological systems such as the reproductive organs, the growth-oriented systems and the cardiovascular structures within the body of an animal or human being. Furthermore, there is presently no doubt that the consumption of grains infested with ergotamines or ergopeptines will also directly affect the gastrointestinal system and hence strongly impair not only the health of animals, but also their performances.

BRIEF SUMMARY OF THE INVENTION

The present invention aims to provide enzymes and enzyme preparations as well as genes from which such enzymes and enzyme preparations are derived, which enable the degradation of ergopeptines to less toxic metabolites, in particular ergine.

To solve this object, the invention is essentially characterized in that said enzymes are α/β-hydrolases hydrolytically cleaving ergopeptines in the cyclol ring. The oxazolidin-4-on ring of the ergopeptines is defined as cyclol ring. By enzymatically cleaving ergopeptines in the cyclol ring using an ergopeptine-specific α/β-hydrolase, it has become possible to degrade the ergopeptines to ergine in a multistep reaction partially occurring spontaneously. α/β-hydrolases are members of an enzyme class with different catalytic functions, which, inter alia, are able to attack the cyclol ring of native ergopeptines and degrade the latter to ergine via a secondary lysergic acid amide (ergo hydroxy acid).

According to a further development of the invention, said enzymes are essentially characterized in that they comprise a catalytic triad consisting of a nucleophilic amino acid and histidine and an acidic amino acid, and that the triad is contained in a peptide chain with an α/β-hydrolase fold. A particularly complete enzymatic cleavage will be achieved in that the catalytic triad consists of the nucleophilic amino acid serine, of histidine and one of the acidic amino acids, aspartate or glutamate, and that the triad is contained in a peptide chain with a fold of an ergopeptine-specific α/β-hydrolase. The use of an enzyme comprising the above-defined catalytic triad has enabled the complete enzymatic cleavage of ergopeptines to ergine in a surprising manner. The enzymatic cleavage occurs at the 3'-site of the cyclol ring of ergopeptines, during which hydrolytic cleavage the group of three rings, namely the cyclol ring, the lactam ring and the pyrolidine ring, is cleaved in several steps to finally form ergine, as can be taken from the following reaction scheme.

| R1 | R2 | Ergopeptine |
|---|---|---|
| CH₃ | CH(CH₃)₂ | Ergovaline |
| CH₃ | CH₂C₆H₅ | Ergotamine |
| CH₃ | CH₂CH(CH₃)₂ | α-Ergosine |
| CH(CH₃)₂ | CH(CH₃)₂ | Ergocornine |
| CH(CH₃)₂ | CH₂C₆H₅ | Ergocrystine |
| CH(CH₃)₂ | CH₂CH(CH₃)₂ | α-Ergocryptine |

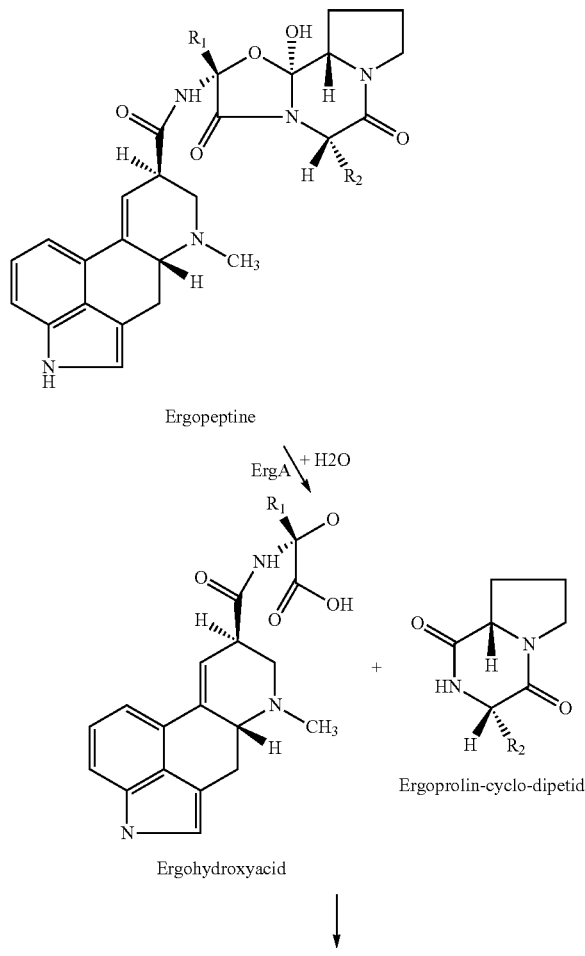

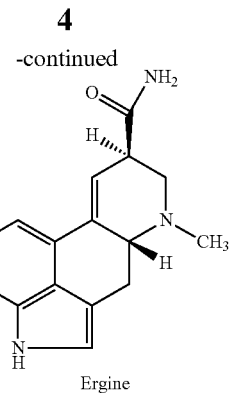

Ergine

According to a further development of the invention, said enzyme is essentially characterized in that the α/β-hydrolase comprises a nucleophilic elbow having the sequence Gly-Gln-Ser-Arg-Asn-Gly. If the α/β-hydrolase comprises a nucleophilic elbow having the sequence Gly-Gln-Ser-Arg-Asn-Gly, a particularly rapid enzymatic degradation of ergopeptine to ergo hydroxy acid will be possible, the latter being spontaneously transformed into ergine. In this case, the nucleophilic elbow is a central element of the α/β-hydrolases. It comprises the catalytically active amino acid with the nucleophilic side chain in a structure having unusual bond angles located in unfavorable regions of the Ramachandran plot (Ollis et al., 1992). The amino acid sequence of the nucleophilic elbow, in the present case Gly-Gln-Ser-Arg-Asn-Gly, is conserved and can, for instance, also be used for classifying α/β-hydrolases (Kourist et al., 2010).

According to a preferred further development of the invention, a complete degradation will be enabled in that said enzyme comprises the sequence ID No. 1. The enzyme comprising the sequence ID No. 1 has turned out to be particularly effective in the catalytic cleavage of ergopeptines to ergine. The nucleophilic amino acid serine assumes a central role in a conserved structure, i.e. the nucleophilic elbow. The nucleophilic elbow is localized between the β5-strand and the consecutive α-helix, and comprises the consensus sequence Sm-X-Nu-X-Sm, wherein Sm is a small amino acid, X is any amino acid, and Nu represents a nucleophilic amino acid. The sequence ID No. 1 is G-Q-S-R-N. The α/β-hydrolase having sequence ID No. 1 belongs to the enzymes that do not require any cofactors for their mode of action.

According to a preferred further development of the invention, said enzyme is characterized in that it comprises at least 96% sequence identity with sequence ID No. 1, wherein the catalytic properties of said enzyme are substantially maintained. In a surprising manner, it could be demonstrated that in addition to the enzyme with sequence ID No. 1, modifications thereof can also be used, and that good results are still possible with the modified enzymes, as was shown by way of the enzyme with sequence ID No. 5.

According to a preferred further development of the invention, said enzyme is characterized in that it comprises an, in particular extended, N- or C-terminal sequence different from the sequence ID No. 1, in particular an enzyme having sequence ID No. 5, and that it exhibits at least 96% sequence identity with sequence ID No. 1. It could be demonstrated in a surprising manner that, in addition to the sequence ID No. 1, a modification width thereof may also be provided, wherein, in particular, the N-terminus can be modified. Especially good results will be achieved if the enzyme with a modified starting sequence exhibits a sequence identity with sequence ID No. 1 of at least 96%.

Enzymes with an N-terminus deviating from the sequence ID No. 1 are equally apt to completely degrade ergotamine.

In order to completely degrade and detoxify ergopeptines, the present invention, furthermore, aims to provide a method for enzymatically transforming ergopeptines.

To solve this object, the method according to the invention is essentially characterized in that the ergopeptines are hydrolytically cleaved in the cyclol ring to primary metabolites.

It turned out in a surprising manner that, following the hydrolytic cleavage of ergopeptines in the cyclol ring to ergot hydroxy acid and ergoproline cyclodipeptide, a spontaneous reaction of these intermediate products to, in particular, ergine and pyruvate takes place. The thus formed reaction products exhibit a toxicity that is significantly reduced, if not negligible, relative to that of the starting product.

In a preferred manner, the method according to the invention is substantially performed such that said cleaving is effected by a nucleophilic attack on the C3'-atom of the cyclol ring. Particularly advantageous and complete results will be achieved in that the nucleophilic attack on the C3'-atom of the cyclol ring is effected by a catalytic triad contained in a peptide chain with an α/β-hydrolase fold and consisting of the nucleophilic amino acid serine, of histidine and one of the acidic amino acids, aspartate or glutamate. Such a process control allows for the achievement of a rapid and complete degradation of the ergopeptines to primary metabolites, which, as in correspondence with a preferred further development of the invention, are further converted into ergine. Such a reaction, according to a preferred further development of the invention, is effected by a spontaneous reaction, to which end the ambient conditions are selected such that the intermediate products of the degradation are directly and completely further transformed into ergine.

As in correspondence with a further development of the invention, the method is performed such that the further reaction of the primary metabolites formed by the hydrolytic cleavage with the α/β-hydrolase is effected by enzymes occurring in the reaction medium. Such a process control uses the enzymes always present in natural surroundings, which are surprisingly able to completely degrade the primary metabolites to ergine.

The present invention, moreover, aims to provide a method for producing ergopeptine-metabolizing enzymes. To solve this object, the method according to the invention is performed such that a gene for an enzyme coding according to the invention is cloned in an expression vector, transformed into prokaryotic and/or eukaryotic host cells, and expressed in a host cell.

Such a procedure enables the provision of high enzyme concentrations which are able to completely convert to ergine six ergopeptines, namely ergotamine, ergovaline, ergocomine, ergocristine, ergocryptine and ergosine as well their respective isomeric forms, namely ergotaminine, ergovalinine, ergocominine, ergocristinine, ergocryptinine and ergosinine. In this case, a gene having sequence ID No. 2, 4 or 6 is preferably used to enable a further increase in the enzyme combinations formed.

Particularly high enzyme activities will be achieved according to the present invention, if the method is performed such that the gene is transformed into, and expressed in, one of the microorganisms selected from Pichia pastoris, E. coli or Bacillus subtilis as host cell. The name Pichia pastoris used in the present application is a synonym for the name Komagataella pastoris, Pichia pastoris being the older and Komagataella pastoris being the systematically newer name (Yamada et al., 1995).

An even further increase in the enzyme activity will be achieved in that the method is performed such that the enzyme having sequence ID No. 1, in particular the his-tagged enzyme having sequence ID No. 5, is purified by affinity chromatography. A purified enzyme having sequence ID No. 5 not only enables the complete conversion of ergopeptines into ergine, but such a purified enzyme will, in particular, display an especially high catalytic activity, in particular in a pH range between about 6 and about 9.

According to a preferred further development of the method, the first step of the reaction is carried out such that the cyclol ring is cleaved by the enzyme of sequence ID No. 1. Such a method control enables the ergopeptines to be almost completely converted into metabolites having a low vasoconstrictive activity.

The enzyme preparation according to the present invention is preferably applied in a feed or silage additive. Such use enables the detoxification of the ergopeptines present on feed or silage additives, partially prior to feeding and partially in the gastrointestinal tracts of the animals, merely by admixing said enzyme preparation.

BRIEF DESCRIPTION OF THE SEVERAL VIEWS OF THE DRAWINGS(S)

Figure 2E:
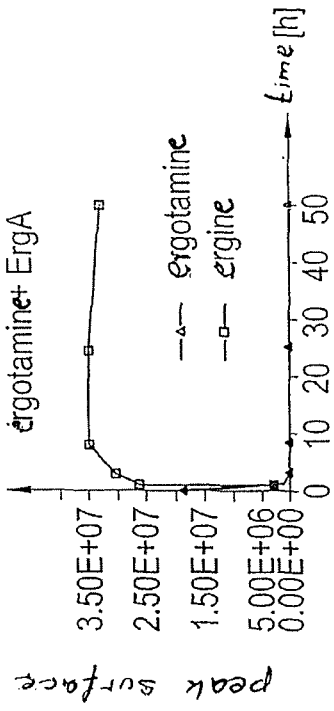
Figure 2F:
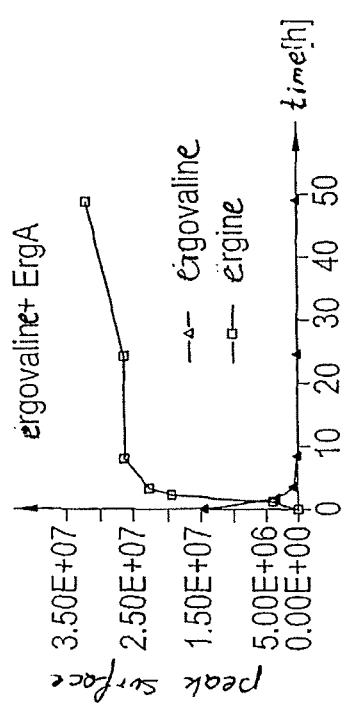
Figure 2G:
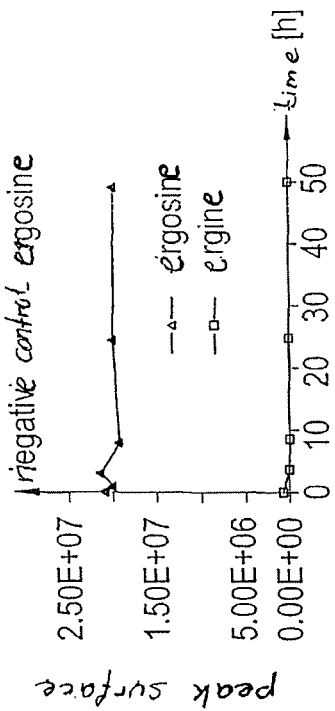
Figure 2H:
Figure 3:
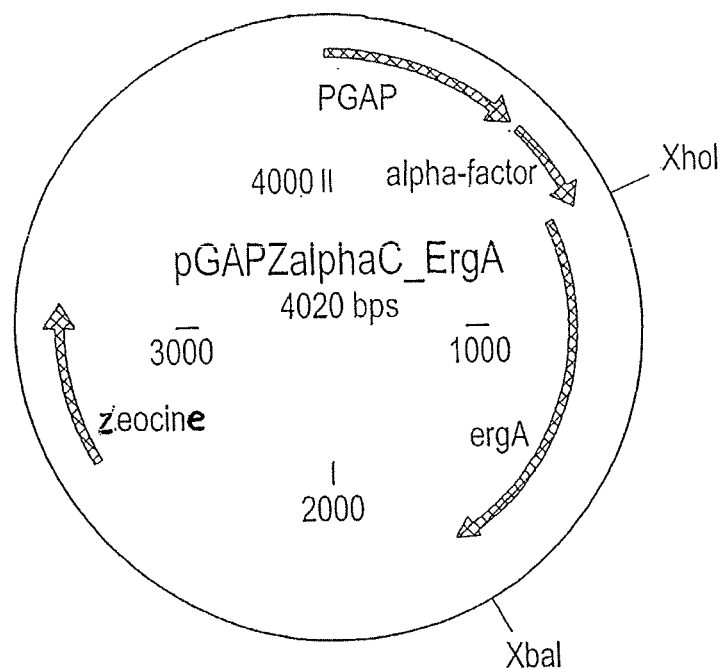
Figure 4:
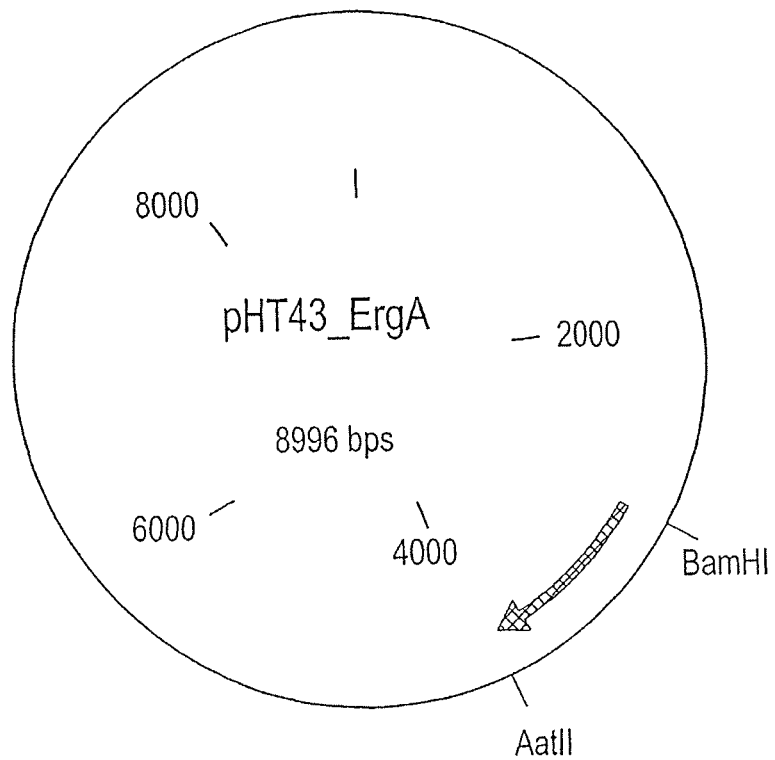

In the following, the invention will be explained in more detail by way of exemplary embodiments and Figures. Therein, FIG. 1 illustrates the kinetics of the reaction of ergotamine to ergine with the enzyme having sequence ID No. 1;

FIG. 2 illustrates the reaction of the ergopeptines ergocomine, ergocryptine, ergosine, ergovaline and ergotamine by the enzyme of sequence ID No. 1 with the exemplary negative controls for ergocryptine and ergosine, wherein FIG. 2a illustrates the reaction of ergocomine by the enzyme of sequence ID No. 1, FIG. 2b illustrates the reaction of ergocristine by the enzyme of sequence ID No. 1, FIG. 2c illustrates the reaction of ergocryptine by the enzyme of sequence ID No. 1, FIG. 2d illustrates the reaction of ergosine by the enzyme of sequence ID No. 1, FIG. 2e illustrates the reaction of ergovaline by the enzyme of sequence ID No. 1, FIG. 2e illustrates the reaction of ergotamine by the enzyme of sequence ID No. 1, FIG. 2f illustrates the negative control ergocryptine and FIG. 2g illustrates the negative control ergosine;

FIG. 3 is an illustration of the P. pastoris expression vector pGAPZ alphaC with the gene sequence ID No. 2; and FIG. 4 is an illustration of the B. subtilis expression vector pET43 with the gene sequence ID No. 2.

DETAILED DESCRIPTION OF THE INVENTION

Example 1

Determination of the Catalytic Activity of the Enzyme with the Sequence ID No. 1

The gene with the sequence ID No. 2, which codes for an α/β-hydrolase comprising a catalytic triad of S94-D234-H270, was cloned into the expression vector pET28a(+) by applying standard methods, transformed and expressed in *E. coli*. Following the expression in *E. coli* BL21(DE3), the his-tagged enzyme was purified by affinity chromatography. The enzyme concentration was determined using a Pierce BSA Protein Assay Kit, and the enzyme was used in activity assays. The assays were carried out in 50 mM sodium phosphate buffer (pH 7.0) at 25° C.

In the context of the detoxification assays, enzyme concentrations of 0.079 µg/ml and ergotamine concentrations of 5 mg/kg were used.

A further assay for reacting the six ergopeptines, namely ergotamine, ergovaline, ergocomine, ergocristine, ergocryptine or ergosine, and their respective isomeric forms, namely ergotaminine, ergovalinine, ergocominine, ergocristinine, ergocryptinine and ergosinine, used 1.58 µg/ml of the enzyme with sequence ID No. 1 and 10 mg/kg ergotamine, or the equimolar (summation) concentrations of the remaining ergopeptines or their epimers. The results are indicated in FIG. 2.

The samples were analyzed using HPLC-FLD or HPLC-MS/MS, each by analytically determining the respective concentration of the sum of the respective epimers. Simultaneously with the determination of the ergopeptine concentration during the enzymatic reaction, the formation of the ergo hydroxy acid (metabolite 1) and of the ergoproline cyclodipeptide (metabolite 2) was observed. During the continued reaction course, the conversion of metabolite 1 to ergine was detected.

FIG. 1 exemplarily shows the kinetics of the reaction of ergotamine with sequence ID No. 1. During said reaction, slight amounts of an instable intermediate product were detected, and the end production of the reaction was ergine. From FIG. 1, it is apparent that an almost complete degradation of ergotamine to ergine by sequence ID No. 1 occurred within 4 hours. The reaction courses of all other ergopeptines, namely ergovaline, ergocomine, ergocristine, ergocryptine or ergosine, as well as their respective isomeric forms, namely ergovalinine, ergocominine, ergocristinine, ergocryptinine and ergosinine, are comparable.

Example 2

Identification of the N-terminus of the enzyme with the sequence ID No. 1 To identify the N-terminus of the enzyme with sequence ID No. 1, the genes having sequences ID No. 2 and ID No. 6 were cloned into PET28a(+) and transformed into *E. coli* using standard methods.

Following the expression, the bacteria cells were taken up in 50 mM sodium phosphate buffer and lyzed using a French press (20,000 psi). The lysates were used in dilutions of 1:10, 1:100 and 1:1000 in degradation batches of 5 mg/kg ergotamine. The batches were incubated at 25° C., and the samples were analyzed using HPLC-FLD.

The results of the degradation test indicated that both of the enzymes were able to transform ergotamine. However, the enzyme with the shorter nucleotide sequence displayed a significantly higher activity, this variant thus having been able to completely transform ergotamine even in the 1:1000 dilution, the longer variant displaying only little activity already in the 1:100 dilution.

Example 3

Determination of the Temperature Range of the Activity, and the Temperature Stability, of the Enzyme with the Sequence ID No. 1

In order to determine the optimum temperature for the activity of the enzyme with the sequence ID No. 1, 0.1 µg/ml enzyme was incubated with 5 mg/kg ergotamine in Teorell-Stenhagen universal buffer (pH 9.0) at varying temperatures ranging from 10° C. to 50° C. The enzyme displayed activity in a range of 10° C. to 35° C. with an optimum at 35° C., based on the starting speed.

In order to determine the temperature stability, the enzyme was incubated for 1 h at varying temperatures ranging from 10° C. to 60° C. After this, the enzyme solutions were incubated at concentrations of 0.1 µg/ml in Teorell-Stenhagen universal buffer (pH 7.0) with 0.1 mg/ml BSA and 5 mg/kg ergotamine at 25° C. The results indicate that the enzyme is stable up to a temperature of 30° C., still displaying some activity after incubation at 40° C., yet showing a decrease of activity between 35° and 40° C. To sum up, it has turned out that the enzyme with the sequence ID No. 1 substantially shows the temperature optimum at the temperature conditions found in the gastrointestinal tract.

Example 4

Determination of the pH Optimum of the Activity, and the pH Stability, of the Enzyme with the Sequence ID No. 1

In order to determine the optimum pH range for the activity of ErgA, 0.1 µg/ml enzyme was incubated with 5 mg/kg ergotamine at varying pH values using Teorell-Stenhagen universal buffer at 25° C. Said buffer was chosen, since the combination of citrate, phosphate and borate allows for the adjustment of the same buffer capacity in a range of pH 2 to pH 12 by hydrochloric acid. The enzyme displayed activity in a range of pH 6 to pH 11 with a small activity plateau at pH 8 to pH 9.

In order to determine the pH stability, the enzyme was incubated for 1 h at 25° C. at varying pH values ranging from pH 2 to pH 12. After this, the enzyme solutions in concentrations of 0.1 µg/ml were incubated with 0.1 mg/ml BSA and 5 mg/kg ergotamine in Teorell-Stenhagen universal buffer (pH 7.0) at 25° C. Also in this case an activity plateau appeared, this time in the range of pH 6 to pH 9, with a strongly decreasing activity outside this range. The activity in this range ensures the technological application of the enzyme with the sequence ID No. 1 as a feed additive.

Example 5

Expression of the Enzyme with the Sequence ID No. 1 in *Picha pastoris*

The gene with the sequence ID No. 2 was cloned into pGAPZ alpha C, transformed into *P. pastoris*, and expressed using standard methods. The expression vector pGAPZ alphaC with the gene having the sequence ID No. 2 is illustrated in FIG. 3. A degradation assay was carried out in 50 mM sodium phosphate buffer (pH 7.0) with 5 mg/kg ergotamine at 25° C. From the culture supernatant, a 1:100 dilution was used. The samples were analyzed by HPLC-FLD. Based on the results from SDS-PAGE and degradation assays, an expression of the enzyme with the sequence ID No. 1 in the culture supernatant could be confirmed.

Example 6

Expression of the Enzyme with the Sequence ID No. 1 in *Bacillus subtilis*

The gene with the sequence ID No. 2 was cloned into pHT43, transformed into *B. subtilis*, and expressed using standard methods. The expression vector pHT43 with the gene having the sequence ID No. 2 is illustrated in FIG. 4. A degradation assay was carried out in 50 mM sodium phosphate buffer (pH 7.0) with 5 mg/kg ergotamine at 25° C. From the culture supernatant, a 1:10 dilution was used. The samples were analyzed by HPLC-FLD. Based on the results from SDS-PAGE and degradation assays, an expression of ErgA in the culture supernatant could be confirmed.

Example 7

Degradation Assay in the Rumen Model

The activity of the ergot alkaloid-degrading enzyme of the enzyme with the sequence ID No. 1 was tested in an in-vitro rumen model. To this end, fresh rumen juice was diluted 1:1 using a solution consisting of synthetic rumen juice, hay and a cereal mixture of wheat, maize and soy. To demonstrate the reaction of the ergopeptines, a batch was supplemented with the enzyme of sequence ID No. 1 (1 µg/ml) and 5 mg/kg ergotamine. Fermentation tubes were used over septums, and the batches were incubated in water bath at 39° C. Analytics by means of HPLC/ESI-MS/MS showed that ergotamine had been completely converted into ergine and lysergic acid in the rumen model.

LITERATURE

MARTINKOVA, L., KREN, V., CVAK, L., OVESNA, M. & PREPECHALOVA, I. 2000. Hydrolysis of lysergamide to lysergic acid by *Rhodococcus equi* A4. *J. Biotechnol.*, 84, 63-66.

KOURIST, R., JOCHENS, H., BARTSCH, S., KUIPERS, R., PADHI, S. K., GALL, M., BÖTTCHER, D., JOOSTEN, H.-J. & BORNSCHEUER, U. T. 2010, The α/β Hydrolase Fold 3DM Database (ABHDB) as a Tool for Protein Engineering. *Chem Bio Chem*, 11, 1635-1643.

OLLIS, D. L., CHEAH, E., CYGLER, M., DIJKSTRA, B., FROLOW, F., FRANKEN, S. M., HAREL, M., REMINGTON, S. J., SILMAN, I. & SCHRAG, J. 1992. The alpha/beta hydrolase fold. Protein Eng., 5, 197-211.

SCHARDL C. L., PANACCIONE D. G. & TUDZYNSKI P. 2006. Ergot Alkaloids—Biology and Molecular Biology. *The Alkaloids,* 63, 45-86.

YAMADA Y., MATSUDA M., MAEDA K. & MIKATA K. 1995. The Phylogenetic Relationship of Methanol-assimilating Yeasts Based on the Partial Sequence of 18S and 26S Ribosomal RNAs: The Proposal of Komagataella Gen. Nov. (Saccharomycetaceae). *Biosci. Biotech. Biochem.*, 59(3), 439-444.

The invention claimed is:

1. A method for hydrolysis of ergopeptine comprising contacting α/β-hydrolase with ergopeptine wherein the C3-N bond of the oxazolidine-4-one ring is cleaved to a primary metabolite, wherein the α/β-hydrolase has at least 96% sequence identity with SEQ ID NO: 1.

2. The method according to claim 1, wherein ergine is formed in a subsequent reaction of the primary metabolites.

* * * * *

```
SEQUENCE LISTING

<160> NUMBER OF SEQ ID NOS: 7

<210> SEQ ID NO 1
<211> LENGTH: 309
<212> TYPE: PRT
<213> ORGANISM: Rhodococcus erythropolis

<400> SEQUENCE: 1

Met Pro Leu Val Val Leu Ser Asp Gly Thr Arg Ile His Val Glu Thr
1               5                   10                  15

Ser Gly Asn Gly Val Pro Ala Leu Val Pro Cys Val Gly Ser Ser Val
            20                  25                  30

Pro Phe Glu Arg Thr Phe Gly Glu Glu Leu Lys Thr Asp Ile Gln Tyr
        35                  40                  45

Asn Phe Val Glu Val Arg Gly Thr Ser Arg Ser Asp Gly Glu Pro Ser
    50                  55                  60

Glu Val Ala Ser Leu Asp Arg Ile Ser Asp Asp Leu Glu Glu Val Arg
65                  70                  75                  80

Gln Leu Leu Gly Leu Asp Lys Val Ile Ala Leu Gly Gln Ser Arg Asn
                85                  90                  95

Gly Met Met Ala Ala His Tyr Ala Gln Lys Tyr Pro Asn Ser Val Leu
            100                 105                 110

His Leu Val Thr Ile Gly Thr Pro Ala Ser Leu Ser Met Ile Lys Asn
        115                 120                 125

Glu Glu Tyr Trp Asn Ala Phe Ala Asp Asp Glu Arg Lys Arg Leu Arg
    130                 135                 140

Ala Glu Asn Asp Ala Ala Met Glu Arg Glu Gly Leu Leu Asp Leu Asp
145                 150                 155                 160

Asn Leu Asn Thr Ala Glu Lys Ile Val Arg Leu Phe Asp Leu Glu Gly
                165                 170                 175

Ala Val Tyr Phe Tyr Asp Pro Thr Thr Leu Met Asn Asp Trp Trp Asp
            180                 185                 190

Ala Ser Leu Leu Ser Arg Thr Phe Glu Val Val Met Ala Ser Asn Met
```

```
              195                 200                 205
Gly Trp Ala Asp Phe Asp Leu Val Gln Thr Leu Gln Asn Ser Asp Val
    210                 215                 220

Pro Ala Phe Val Thr Phe Gly Lys Tyr Asp Phe Met Val Ser Pro Leu
225                 230                 235                 240

Pro Lys Pro Gly Asn Pro Val Asp Gly Lys Ala Gly Leu Phe Glu Asp
                245                 250                 255

Ile Pro Gly Val Arg Val Glu Val Phe Glu Lys Ser Gly His Phe Pro
            260                 265                 270

Tyr Trp Glu Gln Glu Gln Phe Ala Arg Arg Tyr Arg Asp Trp Val
        275                 280                 285

Ala Thr Leu Pro Glu Ser Ala Val Arg Ala Ala Glu Ala Met Thr Pro
    290                 295                 300

Asn Gly Ile Arg Gln
305

<210> SEQ ID NO 2
<211> LENGTH: 930
<212> TYPE: DNA
<213> ORGANISM: Rhodococcus erythropolis

<400> SEQUENCE: 2
atgccattgg tggttctgag cgacggcaca cgcattcacg tcgaaacttc aggcaacggc      60
gtccctgcgc ttgttccatg cgtgggatcg agcgttccgt tcgagcggac gttcggtgag     120
gaattgaaga cggatattca gtacaacttc gtcgaggtcc gcggtacctc caggtccgac     180
ggcgaaccga gtgaggtcgc ctcactcgat cgtatttccg acgacctcga agaggtccgt     240
cagttgttgg gttttggacaa ggtcatcgca ctcggccagt cgcgtaacgg catgatggcc     300
gctcactacg cgcagaagta tccgaattcg gtcctacacc tggtaaccat cggcacccct     360
gcgtctttga gtatgatcaa gaacgaagaa tactggaacg cgttcgcaga cgacgagcgt     420
aaacgcctcc gcgctgaaaa acgacgcggcg atggagcgcg agggtctcct cgaccttgac     480
aacctgaata ctgccgaaaa gatcgttcgc ctcttcgatc ttgaaggcgc agtgtacttc     540
tacgatccaa cgacactcat gaatgattgg tgggacgctt cacttctcag ccggacattc     600
gaagtcgtca tggcgtcgaa tatggggttgg gcagacttcg acctcgttca aacactgcag     660
aattctgatg tcccccgcttt cgtaacgttc ggaaagtacg acttcatggt ctccccgctg     720
ccgaaaccag gaaatccggt tgacggaaaa gccggcctct cgaagatat tccgggtgtc     780 cgggtagagg tcttcgagaa gagtgggcac ttcccgtatt gggagcagga acaggaattt     840
gctcgccgct atcgcgattg ggtcgcaacc cttccggaat ccgctgtacg cgctgcagaa     900
gctatgacgc caatggcat tcggcagtga                                       930

<210> SEQ ID NO 3
<211> LENGTH: 319
<212> TYPE: PRT
<213> ORGANISM: Rhodococcus erythropolis

<400> SEQUENCE: 3

Met Ala Arg Pro Lys Arg Arg Ser Ala Met Pro Leu Val Val Leu
1               5                   10                  15

Ser Asp Gly Thr Arg Ile His Val Glu Thr Ser Gly Asn Gly Val Pro
            20                  25                  30

Ala Leu Val Pro Cys Val Gly Ser Ser Val Pro Phe Glu Arg Thr Phe
        35                  40                  45
```

Gly Glu Glu Leu Lys Thr Asp Ile Gln Tyr Asn Phe Val Glu Val Arg
        50                  55                  60

Gly Thr Ser Arg Ser Asp Gly Glu Pro Ser Glu Val Ala Ser Leu Asp
65                  70                  75                  80

Arg Ile Ser Asp Asp Leu Glu Val Arg Gln Leu Leu Gly Leu Asp
                85                  90                  95

Lys Val Ile Ala Leu Gly Gln Ser Arg Asn Gly Met Met Ala Ala His
                100                 105                 110

Tyr Ala Gln Lys Tyr Pro Asn Ser Val Leu His Leu Val Thr Ile Gly
                115                 120                 125

Thr Pro Ala Ser Leu Ser Met Ile Lys Asn Glu Glu Tyr Trp Asn Ala
        130                 135                 140

Phe Ala Asp Asp Glu Arg Lys Arg Leu Arg Ala Glu Asn Asp Ala Ala
145                 150                 155                 160

Met Glu Arg Glu Gly Leu Leu Asp Leu Asp Asn Leu Asn Thr Ala Glu
                165                 170                 175

Lys Ile Val Arg Leu Phe Asp Leu Glu Gly Ala Val Tyr Phe Tyr Asp
                180                 185                 190

Pro Thr Thr Leu Met Asn Asp Trp Trp Asp Ala Ser Leu Leu Ser Arg
        195                 200                 205

Thr Phe Glu Val Val Met Ala Ser Asn Met Gly Trp Ala Asp Phe Asp
210                 215                 220

Leu Val Gln Thr Leu Gln Asn Ser Asp Val Pro Ala Phe Val Thr Phe
225                 230                 235                 240

Gly Lys Tyr Asp Phe Met Val Ser Pro Leu Pro Lys Pro Gly Asn Pro
                245                 250                 255

Val Asp Gly Lys Ala Gly Leu Phe Glu Asp Ile Pro Gly Val Arg Val
                260                 265                 270

Glu Val Phe Glu Lys Ser Gly His Phe Pro Tyr Trp Glu Gln Glu Gln
        275                 280                 285

Glu Phe Ala Arg Arg Tyr Arg Asp Trp Val Ala Thr Leu Pro Glu Ser
        290                 295                 300

Ala Val Arg Ala Ala Glu Ala Met Thr Pro Asn Gly Ile Arg Gln
305                 310                 315

<210> SEQ ID NO 4
<211> LENGTH: 960
<212> TYPE: DNA
<213> ORGANISM: Rhodococcus erythropolis

<400> SEQUENCE: 4
atggctcgcc ccaagagaag gagatctgcc atgccattgg tggttctgag cgacggcaca      60
cgcattcacg tcgaaacttc aggcaacggc gtccctgcgc ttgttccatg cgtgggatcg     120
agcgttccgt tcgagcggac gttcggtgag gaattgaaga cggatattca gtacaacttc     180
gtcgaggtcc gcggtaccct caggtccgac ggcgaaccga gtgaggtcgc ctcactcgat     240
cgtatttccg acgacctcga gaggtccgt cagttgttgg gtttggacaa ggtcatcgca     300
ctcggccagt cgcgtaacgg catgatggcc gctcactacg cgcagaagta tccgaattcg     360
gtcctacacc tggtaaccat cggcaccct gcgtctttga gtatgatcaa gaacgaagaa     420
tactggaacg cgttcgcaga cgacgagcgt aaacgcctcc gcgctgaaaa cgacgcggcg     480
atggagcgcg agggtctcct cgaccttgac aacctgaata ctgccgaaaa gatcgttcgc     540
ctcttcgatc ttgaaggcgc agtgtacttc tacgatccaa cgacactcat gaatgattgg     600

-continued

```
tgggacgctt cacttctcag ccggacattc gaagtcgtca tggcgtcgaa tatgggttgg    660
gcagacttcg acctcgttca aacactgcag aattctgatg tccccgcttt cgtaacgttc    720
ggaaagtacg acttcatggt ctccccgctg ccgaaaccag gaaatccggt tgacggaaaa    780
gccggcctct tcgaagatat tccgggtgtc cgggtagagg tcttcgagaa gagtgggcac    840
ttcccgtatt gggagcagga acaggaattt gctcgccgct atcgcgattg gtcgcaacc     900 cttccggaat ccgctgtacg cgctgcagaa gctatgacgc ccaatggcat tcggcagtga    960
```

<210> SEQ ID NO 5
<211> LENGTH: 316
<212> TYPE: PRT
<213> ORGANISM: Rhodococcus erythropolis

<400> SEQUENCE: 5

Met Gly Pro Leu Val Val Leu Ser Asp Gly Thr Arg Ile His Val Glu
1               5                   10                  15

Thr Ser Gly Asn Gly Val Pro Ala Leu Val Pro Cys Val Gly Ser Ser
            20                  25                  30

Val Pro Phe Glu Arg Thr Phe Gly Glu Glu Leu Lys Thr Asp Ile Gln
        35                  40                  45

Tyr Asn Phe Val Glu Val Arg Gly Thr Ser Arg Ser Asp Gly Glu Pro
    50                  55                  60

Ser Glu Val Ala Ser Leu Asp Arg Ile Ser Asp Leu Glu Val
65                  70                  75                  80

Arg Gln Leu Leu Gly Leu Asp Lys Val Ile Ala Leu Gly Gln Ser Arg
                85                  90                  95

Asn Gly Met Met Ala Ala His Tyr Ala Gln Lys Tyr Pro Asn Ser Val
            100                 105                 110

Leu His Leu Val Thr Ile Gly Thr Pro Ala Ser Leu Ser Met Ile Lys
        115                 120                 125

Asn Glu Glu Tyr Trp Asn Ala Phe Ala Asp Asp Glu Arg Lys Arg Leu
    130                 135                 140

Arg Ala Glu Asn Asp Ala Ala Met Glu Arg Glu Gly Leu Leu Asp Leu
145                 150                 155                 160

Asp Asn Leu Asn Thr Ala Glu Lys Ile Val Arg Leu Phe Asp Leu Glu
                165                 170                 175

Gly Ala Val Tyr Phe Tyr Asp Pro Thr Thr Leu Met Asn Asp Trp Trp
            180                 185                 190

Asp Ala Ser Leu Leu Ser Arg Thr Phe Glu Val Val Met Ala Ser Asn
        195                 200                 205

Met Gly Trp Ala Asp Phe Asp Leu Val Gln Thr Leu Gln Asn Ser Asp
    210                 215                 220

Val Pro Ala Phe Val Thr Phe Gly Lys Tyr Asp Phe Met Val Ser Pro
225                 230                 235                 240

Leu Pro Lys Pro Gly Asn Pro Val Asp Gly Lys Ala Gly Leu Phe Glu
                245                 250                 255

Asp Ile Pro Gly Val Arg Val Glu Val Phe Glu Lys Ser Gly His Phe
            260                 265                 270

Pro Tyr Trp Glu Gln Glu Gln Glu Phe Ala Arg Arg Tyr Arg Asp Trp
        275                 280                 285

Val Ala Thr Leu Pro Glu Ser Ala Val Arg Ala Ala Glu Ala Met Thr
    290                 295                 300

Pro Asn Gly Ile Arg Gln His His His His His His

<210> SEQ ID NO 6
<211> LENGTH: 951
<212> TYPE: DNA
<213> ORGANISM: Rhodococcus erythropolis

<400> SEQUENCE: 6

```
atgggcccat tggtggttct gagcgacggc acacgcattc acgtcgaaac ttcaggcaac    60
ggcgtccctg cgcttgttcc atgcgtggga tcgagcgttc cgttcgagcg gacgttcggt   120
gaggaattga agacggatat tcagtacaac ttcgtcgagg tccgcggtac ctccaggtcc   180
gacggcgaac cgagtgaggt cgcctcactc gatcgtattt ccgacgacct cgaagaggtc   240
cgtcagttgt tgggtttgga caaggtcatc gcactcggcc agtcgcgtaa cggcatgatg   300
gccgctcact acgcgcagaa gtatccgaat tcggtcctac acctggtaac catcggcacc   360
cctgcgtctt tgagtatgat caagaacgaa gaatactgga acgcgttcgc agacgacgag   420
cgtaaacgcc tccgcgctga aaacgacgcg gcgatggagc gcgagggtct cctcgacctt   480
gacaacctga atactgccga aaagatcgtt cgcctcttcg atcttgaagg cgcagtgtac   540
ttctacgatc aacgacact catgaatgat tggtgggacg cttcacttct cagccggaca   600
ttcgaagtcg tcatggcgtc gaatatgggt tgggcagact tcgacctcgt tcaaacactg   660
cagaattctg atgtccccgc tttcgtaacg ttcggaaagt acgacttcat ggtctccccg   720
ctgccgaaac aggaaatcc ggttgacgga aaagccggcc tcttcgaaga tattccgggt   780
gtccgggtag aggtcttcga gaagagtggg cacttcccgt attgggagca ggaacaggaa   840
tttgctcgcc gctatcgcga ttgggtcgca accttccgg aatccgctgt acgcgctgca   900
gaagctatga cgcccaatgg cattcggcag catcaccatc accatcactg a             951
```

<210> SEQ ID NO 7
<211> LENGTH: 6
<212> TYPE: PRT
<213> ORGANISM: Rhodococcus erythropolis

<400> SEQUENCE: 7

Gly Gln Ser Arg Asn Gly
1               5